United States Patent [19]

Fertel et al.

[11] Patent Number: 5,380,926
[45] Date of Patent: Jan. 10, 1995

[54] METHOD OF MAKING 3-METHOXY-2,4,5-TRIFLUOROBENZOIC ACID

[75] Inventors: Lawrence B. Fertel, Williamsville; William S. Derwin, Buffalo, both of N.Y.

[73] Assignee: Occidental Chemical Corporation, Niagara Falls, N.Y.

[21] Appl. No.: 218,403

[22] Filed: Mar. 28, 1994

[51] Int. Cl.$^6$ .............................................. C07C 65/00
[52] U.S. Cl. ................................................... 562/474
[58] Field of Search ............................................ 562/474

[56] References Cited

U.S. PATENT DOCUMENTS

| | | | |
|---|---|---|---|
| 3,013,054 | 12/1961 | Richter | 562/474 |
| 3,210,414 | 5/1965 | Hanna | 562/474 |
| 4,831,190 | 5/1989 | Ataka | 562/474 |
| 5,194,666 | 3/1993 | Sedlak | 562/474 |
| 5,233,082 | 8/1993 | Fertel | 562/451 |

FOREIGN PATENT DOCUMENTS

| | | |
|---|---|---|
| 747232 | 9/1966 | Canada . |
| 1006235 | 1/1989 | Japan . |
| -1268662 | 10/1989 | Japan . |
| 01268662A2 | 10/1989 | Japan . |
| 03279348A2 | 12/1991 | Japan . |

*Primary Examiner*—Paul J. Killos
*Attorney, Agent, or Firm*—Wayne A. Jones; Richard D. Fuerle

[57] ABSTRACT

Disclosed is a method of making 3-methoxy-2,4,5-trifluorobenzoic acid. A tetrafluorophthalimide is reacted with an alkali metal hydroxide to produce a mixture of alkali metal salts of 4-hydroxy-3,5,6-trifluoro-N-alkylphthalamic acid and 3-hydroxy-2,4,5-trifluoro-N-alkylbenzamide. Those products are reacted with a methylating agent to produce 4-methoxy-3,5,6-trifluoro-N-alkylphthalamic acid and 3-methoxy-2,4,5-trifluoro-N-alkylbenzamide. Those products are reacted with an acid to produce 4-methoxy-3,5,6-trifluorophthalic acid and 3-methoxy-2,4,5-trifluorobenzoic acid. Finally, the 4-methoxy-3,5,6-trifluorophthalic acid is reacted with a decarboxylating agent to produce additional 3-methoxy-2,4,5-trifluorobenzoic acid.

20 Claims, No Drawings

METHOD OF MAKING 3-METHOXY-2,4,5-TRIFLUOROBENZOIC ACID

BACKGROUND OF THE INVENTION

This invention relates to a method of making 3-methoxy2,4,5-trifluorobenzoic acid (MTBA). In particular, it relates to a series of at least four reaction steps for producing MTBA which proceed from a tetrafluorophthalamide to salts of 4-hydroxy-3,5,6-trifluoro-N-alkylphthalamic acid and 3-hydroxy-2,4,5-trifluoro-N-alkylbenzamide to 4-methoxy-3,5,6-trifluoro-N-alkylphthalamic acid and 3-methoxy-2,4,5-trifluoro-N-alkylbenzamide to 4-methoxy-3,5,6-trifluorophthalic acid and MTBA, then to all MTBA.

MTBA is useful as an intermediate in preparing quinolone antibacterials. MTBA is now being made by a process which first involves preparing 4-hydroxy-3,5,6-trifluoro-N-substituted phthalamic acid (HTPA). (See U.S. Pat. No. 5,233,082, herein incorporated by reference.) The HTPA is decarboxylated and methylated to produce MTBA. While that process works very well, for economic reasons it has become desirable to identify other processes for making MTBA.

SUMMARY OF THE INVENTION

We have discovered an alternative process for making MTBA which begins with a tetrafluorophthalamide. While in the prior process for making MTBA decarboxylation occurred prior to methylation, in the process of this invention methylation occurs prior to decarboxylation.

DESCRIPTION OF THE PREFERRED EMBODIMENT

The starting material for the process of this invention is a tetrafluorophthalimide having the general formula

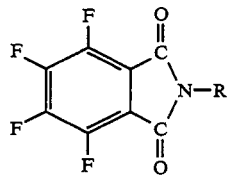

where R is alkyl to $C_8$, cycloalkyl from $C_3$ to $C_8$, or aryl from $C_6$ to $C_{12}$ and is preferably methyl or phenyl as these compounds are less expensive and are easier to work with. This starting material can be produced from tetrachlorophthalic anhydride, a commercially available material sold, for example, by Monsanto as "TETRATHAL ®." The tetrachlorophthalic anhydride reacts with an amine, $RNH_2$, to produce the corresponding imide. Reaction of the imide with fluorinating agents such as, for example, potassium fluoride, produces the starting material of this invention, the tetrafluorophthalimide.

HYDROXYLATION

In the first step of the process of this invention, an aqueous solution is prepared of an alkali metal base and a tetrafluorophthalimide. Preferably, a solution is prepared of the base and the tetrafluorophthalimide is added to that solution. Sodium hydroxide and potassium hydroxide are the preferred bases as they are inexpensive and sodium hydroxide is particularly preferred as it is the less expensive. The solution of the base can be from about 5 to about 50 wt % base as less than about a 5 wt % solution may result in incomplete substitution of the hydroxyl for the fluorine on the aromatic ring and more than about a 50 wt % solution of base is unnecessary. Preferably, the solution of the base is about 15 to about 25 wt %. The amount of tetrafluorophthalimide added to the solution of the base can vary from about 5 wt % up to the solubility of the tetrafluorophthalimide in the solution; less than 5 wt % is inefficient. Preferably, the solution of tetrafluorophthalimide is about 10 to about 20 wt %.

The tetrafluorophthalimide reacts with the base to produce a mixture of the salts of 4-hydroxy-3,5,6-trifluoro-N-substituted phthalamic acid (HTPA) and a 3-hydroxy-2,4,5-trifluoro-N-substituted benzamide (HTB) according to the equation

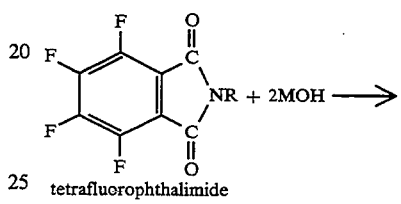
tetrafluorophthalimide

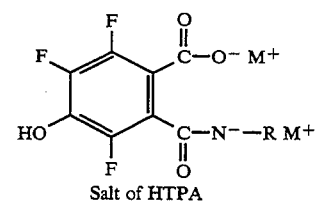
Salt of HTPA

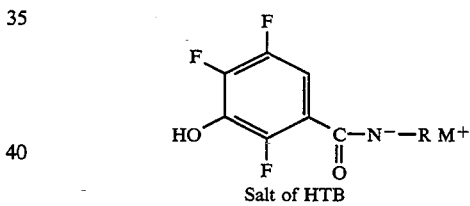
Salt of HTB where M is an alkali metal. This reaction can be performed at from about room temperature to about 130° C. Lower temperatures can be used, but the reaction tends to be too slow and may be incomplete; at temperatures over 130° C., by-products may form. The preferred temperature range is about 75° to about 105° C. The reaction is normally complete after about 2 to about 3 hours and can be followed by gas chromatography (GC) to determine when all the tetrafluorophthalimide has been consumed. The reaction requires at least 2 moles of base per mole of tetrafluorophthalimide and, preferably, about 3 to about 15 moles of base are used per mole of tetrafluorophthalimide to ensure a complete reaction. More than about 15 moles of base per mole of tetrafluorophthalimide is unnecessary and its use means that more base must be subsequently neutralized.

The solution can be neutralized with acid to precipitate a mixture of the HTPA and the HTB. A mineral acid such as hydrochloric acid, sulfuric acid, phosphoric acid, or nitric acid, for example, can be used to neutralize the solution. The pH should be lowered until the precipitate forms. Normally, this requires a pH of about 2.

The precipitate is collected or isolated. This can be accomplished by filtration followed by washing, for example, in cold water. Alternatively, the precipitate can be dissolved in an organic solvent such as ethyl acetate or various ethers to form an organic phase which can be separated from the aqueous phase. The solvent in the organic phase is evaporated to regenerate the precipitate.

OPTIONAL IMIDIZATION

The next step is optional, but is preferably performed as it increases the yield of the product, MTBA. If this step is performed, the solvent is not evaporated and the solution of the HTPA and HTB in the organic solvent is heated, preferably to the boiling point of the organic solvent being used. This results in the formation of a solution of HTB and a 4-hydroxy-3,5,6-trifluoro-N-alkylphthalimide. (Conversion of the HTPA to the corresponding imide can also be accomplished chemically using, for example, acetic anhydride.) The solution is cooled and the solvent evaporated under vacuum to precipitate those compounds.

METHYLATION

In the next step of the process of this invention, the precipitated mixture is dissolved in an aqueous solution of an alkali metal hydroxide such as sodium hydroxide or potassium hydroxide. A pH of about 8 to about 14 is usually adequate to dissolve the solids. To that solution is added about 1 to about 2 equivalents of a methylating agent. A methylating agent is a compound that can replace the hydroxy group on the compounds with a methoxy group. Examples of methylating agents include dimethyl sulfate, methyl chloride, and methyl iodide. Dimethyl sulfate is preferred as it has been found to work very well. The methylation reaction occurs when the solution is heated to a temperature from about room temperature to about 50° C., although higher and lower temperatures are also operable. Methylation produces a solution of a mixture of 4-methoxy-3,5,6-trifluoro-N-alkylphthalamic acid and 3-methoxy-2,4,5-trifluoro-N-alkylbenzamide. (If the 4-hydroxy-3,5,6-trifluoro-N-alkylphthalimide was made in the previous step, 4-methoxy-3,5,6-trifluoro-N-alkylphthalimide will be produced instead of the N-alkylphthalamic acid. The salt form can also be methylated.)

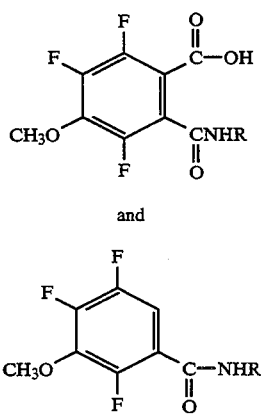

To that solution is added sufficient mineral acid to neutralize it. Almost any mineral acid can be used for this purpose, including hydrochloric, sulfuric, nitric, and phosphoric acid. The compounds are less soluble in the neutralized solution, but still remain in solution.

The 4-methoxy-3,5,6-trifluoro-N-alkylphthalamic acid and 3-methoxy-2,4,5-trifluoro-N-alkylbenzamide are extracted into an organic solvent. Suitable extractants include methylene chloride, ethyl acetate, and diethylether. Ethyl acetate is preferred as it is a convenient solvent to use. The organic solvent is separated from the aqueous solution and is evaporated to produce the solid compounds.

HYDROLYSIS

The solids are dissolved into an aqueous solution of a non-oxidizing mineral acid such as sulfuric acid, hydrochloric acid, or phosphoric acid. Sulfuric acid is preferred as it has been found to work well. The concentration of acid and the temperature of the solution is important in reducing the amount of HTBA which is formed as a by-product. An acid concentration of about 40 to about 60 wt % is preferred, and a temperature of about 125° to about 150° C. is best for minimizing the formation of HTBA. This step is preferably performed for about 20 to about 40 hours. Harsher and milder conditions can result in less yield. This step results in the production of a mixture of 4-methoxy-3,5,6-trifluorophthalic acid and the desired product MTBA:

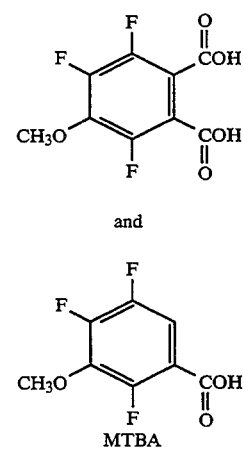

DECARBOXYLATION

In the next step, the 2-methoxy-1,3,4-trifluorophthalic acid is decarboxylated. This can be accomplished by extracting it and the MTBA into an organic solvent as before. The solvent is again evaporated and the solids are collected. The solids are dissolved in a dipolar aprotic solvent such as dimethylsulfoxide (DMSO), dimethylacetamide, or N-methylpyrrolidone (NMP). Dimethylsulfoxide is preferred as it seems to result in the least amount of by-product being produced. This solution is preferably about 10 wt % solids up to saturation. The solution is preferably heated to the temperature of about 150° to about 180° C. which results in the decarboxylation of the 4-methoxy-3,5,6-trifluorophthalic acid by evolution of carbon dioxide to produce the desired product MTBA. The MTBA can be collected by adding water, again extracting into an organic solvent, and evaporating the organic solvent. Purification can be accomplished by standard chromatography or distillation techniques.

The following examples further illustrate this invention. All percentages are by weight.

EXAMPLE 1

Preparation of 4-Hydroxy-3,5,6-trifluoro-N-methylphthalimide

Mixed together were 48 g of a mixture of 4-hydroxy-3,5,6-trifluoro-N-methylphthalamic acid and 3-hydroxy-2,4,5-trifluorobenzamide (preparation given in Example 1 of U.S. Pat. No. 5,233,082) and 200 mL of toluene. The mixture was heated to reflux and water was collected in a Barret trap. After all the water had been collected, the mixture was cooled and the toluene evaporated under vacuum. A total of 40.88 g of solids were collected. This material was assayed as 75% 4-hydroxy-3,5,6-trifluoro-N-methylphthalimide and 11% 3-hydroxy-2,4,5-trifluoro-N-methylbenzamide. For the N-methylphthalimide: $^{19}F$ nuclear magnetic resonance (NMR) (ppm acetone $d_6$): $-136.9$ (m), $-141.5$ (m), $-147.8$ (m).

EXAMPLE 2

Preparation of 4-Methoxy-3,5,6-trifluoro-N-methylphthalimide

The solids from Example 1 were combined with 375 mL of acetone, and 61.08 g of potassium carbonate. With stirring, 55.77 g of dimethyl sulfate was added, and the entire mixture was heated to reflux for 1.5 h. After cooling, 500 mL of water was added and the reaction was acidified with HCl to a pH of 1.0. The mixture was extracted with ethyl acetate and washed with water. After drying with magnesium sulfate and removal of the solvent, 45.08 g of a yellow solid was collected. The solid was assayed as 72% 4-methoxy-3,5,6-trifluoro-N-methylphthalimide. $^{19}F$ NMR (ppm acetone $d_6$): $-133.0$ (m), $-140.8$ (m), $-142.6$ (m), $^1H$ NMR (ppm acetone $d_6$) 3.05 (s), 4.19 (s).

EXAMPLE 3

Preparation of 4-Methoxy-3,5,6-trifluorophthalic Acid

Combined were the solids from Example 2 (45 g) and 200 mL of 40% (w/w) sulfuric acid. The mixture was heated to 145° C. until complete, as monitored by gas chromatography (GC). The reaction was quenched by adding to 400 mL water, and extracted into ethyl acetate (3×100 mL). The combined ethyl acetate layers were washed with water (2×50 mL) and dried with magnesium sulfate. After removal of the solvent under vacuum, 41.75 g of an oil was recovered. The oil was assayed as 68% 4-methoxy-3,5,6-trifluorophthalic acid, along with 10% 4-hydroxy-3,5,6-trifluorophthalic acid.

EXAMPLE 4

In order to determine optional conditions, Example 3 was repeated using different concentrations of sulfuric acid at different temperatures and times. The following table gives the results.

| CONDITIONS | RESULTS | COMMENTS |
| --- | --- | --- |
| 60% H$_2$SO$_4$/125° C/27 h | 67% MTFPA, 28% HTFPA | Too harsh |
| 40% H$_2$SO$_4$/125° C./8 h | No reaction | Too mild |
| 40% H$_2$SO$_4$/150° C./72 h | 67% MTFPA, 28% HTFPA | Too long |
| 40% H$_2$SO$_4$/150° C./22 h | 92% MTFPA, 6% HFTPA, 2% | Best result to date |

EXAMPLE 5

Preparation of 3-Methoxy-2,4,5-trifluorobenzoic Acid In NMP

Combined were 0.34 g of 4-methoxy-3,5,6-trifluorophthalic acid and 3 mL of NMP. The reaction was heated to 150° C. for 24 h. Assay of the reaction by gas chromatography-mass spectroscopy (GCMS) indicated that 3-methoxy-2,4,5-trifluorobenzoic acid was present at a level of 51.0%.

EXAMPLE 6

Preparation of 3-Methoxy-2,4,5-trifluorobenzoic Acid In DMSO

Combined were 0.21 g of 4-methoxy-3,5,6-trifluorophthalic acid and 2 mL of DMSO. The reaction was heated to 150° C. for 24 h. Assay of the reaction by GCMS indicated that 3-methoxy2,4,5-trifluorobenzoic acid was present at a level of 42.6%.

We claim:

1. A method of making 3-methoxy-2,4,5-trifluorobenzoic acid comprising
   (A) reacting a tetrafluorophthalimide with an alkali metal hydroxide to produce a mixture of alkali metal salts of 4-hydroxy-3,5,6-trifluoro-N-alkylphthalamic acid and 3-hydroxy-2,4,5-trifluoro-N-alkylbenzamide;
   (B) reacting the products of step (A) with a methylating agent to replace the hydroxy group on said alkali metal salts with a methoxy group;
   (C) reacting the products of step (B) with a non-oxidizing acid to produce a mixture of 4-methoxy-3,5,6-trifluorophthalic acid and 3-methoxy-2,4,5-trifluoro-benzoic acid; and
   (D) reacting said 4-methoxy-3,5,6-trifluorophthalic acid with a decarboxylating agent to produce 3-methoxy-2,4,5-trifluorobenzoic acid.

2. A method according to claim 1 wherein said alkali metal hydroxide is sodium hydroxide.

3. A method according to claim 1 wherein said methylating agent is dimethyl sulfate.

4. A method according to claim 1 wherein said tetrafluorophthalimide is N-methyl tetrafluorophthalimide.

5. A method according to claim 1 wherein, after step (A) said 4-hydroxy-3,5,6-trifluoro-N-alkylphthalamic acid is converted into 4-hydroxy-3,5,6-trifluoro-N-alkylimide before step (B).

6. A method of making 3-methoxy-2,4,5-trifluorobenzoic acid comprising
   (A) preparing a first aqueous solution of an alkali metal hydroxide and a tetrafluorophthalimide;
   (B) heating said first aqueous solution at a temperature of about room temperature to about 130° C. to produce a mixture of an alkali metal salt of 4-hydroxy-3,5,6-trifluoro-N-alkylphthalamic acid and an alkali metal salt of 3-hydroxy-2,4,5-trifluoro-N-alkylbenzamide;
   (C) adding a mineral acid to said first aqueous solution to form and precipitate a mixture of 4-hydroxy-3,5,6-trifluoro-N-alkylphthalamic acid and 3-hydroxy-2,4,5-trifluoro-N-alkylbenzamide;
   (D) separating said precipitated mixture from said first aqueous solution;
   (E) dissolving said precipitation mixture into a first organic solvent to form an organic solution;

(F) heating said organic solution to convert said 4-hydroxy-3,5,6-trifluoro-N-alkylphthalamic acid into 4-hydroxy-3,5,6-trifluoro-N-alkylphthalimide;

(G) evaporating said first organic solvent to precipitate a mixture of said 4-hydroxyl-N-alkyl-phthalimide and 3-hydroxy-2,4,5-trifluoro-N-alkylbenzamide;

(H) preparing a second aqueous solution by dissolving said precipitated mixture from step (G) and an alkali metal hydroxide in water;

(I) adding about 1 to about 2 equivalents of a methylating agent to said second aqueous solution;

(J) heating said second aqueous solution at a temperature of about room temperature to about 50° C. to produce a solution of a mixture of 4-methoxy-3,5,6-trifluoro-N-alkylphthalimide and 3-methoxy-2,4,5-trifluoro-N-alkylbenzamide;

(K) adding a mineral acid to said second aqueous solution to neutralize it;

(L) extracting said 4-methoxy-3,5,6-trifluoro-N-alkylphthalimide and said 3-methoxy-2,4,5-trifluoro-N-alkylbenzamide into a second organic solvent;

(M) separating said second organic solvent from said second aqueous solution;

(N) evaporating said first organic solvent to produce a mixture of solid 4-methoxy-3,5,6-trifluoro-N-alkylphthalamic acid and 3-methoxy-2,4,5-trifluoro-N-alkylbenzamide;

(O) dissolving said mixture from step (K) and sulfuric acid, hydrochloric acid, or phosphoric acid in water at a temperature of about 125° C. to about 150° C., to produce a third aqueous solution of a mixture of 4-methoxy-3,5,6-trifluorophthalic acid and 3-methoxy-2,4,5-trifluorobenzoic acid;

(P) extracting said mixture of 4-methoxy-3,5,6-trifluorophthalic acid and 3-methoxy-2,4,5-trifluorobenzoic acid into a third organic solvent;

(Q) evaporating said third organic solvent to produce a mixture of solid 4-methoxy-3,5,6-trifluorophthalic acid and 3-methoxy-2,4,5-trifluorobenzoic acid;

(R) forming a fourth aqueous solution by dissolving said mixture from step (N) and a dipolar aprotic decarboxylating solvent in water; and (S) heating said fourth aqueous solution at a temperature of about 150° C. to about 180° C. to decarboxylate said 4-methoxy-3,5,6-trifluorophthalic acid and produce 3-methoxy-2,4,5-trifluorobenzoic acid.

7. A method according to claim 6 wherein said alkali metal hydroxide is sodium hydroxide.

8. A method according to claim 6 wherein said methylating agent is dimethyl sulfate.

9. A method according is to claim 6 wherein said acid sulfuric acid.

10. A method according to claim 6 wherein said decarboxylating agent is dimethylsulfoxide.

11. A method according to claim 6 wherein said tetrafluorophthalamide is N-methyl tetrafluorophthalimide.

12. A method according to claim 6 wherein said tetrafluorophthalamide is N-phenyl tetrafluorophthalimide.

13. A method of making 3-methoxy-2,4,5-trifluorobenzoic acid comprising (A) preparing a first aqueous solution of about 5 to about 50 wt % of an alkali metal hydroxide selected from the group consisting of sodium hydroxide and potassium hydroxide and about 5 wt % to saturation of a tetrafluorophthalimide selected from the group consisting of N-methyl tetrafluorophthalimide and N-phenyl tetrafluorophthalimide;

(B) heating said first aqueous solution at a temperature of about 75° C. to about 105° C. to produce a mixture of an alkali metal salt of 4-hydroxy-3,5,6-trifluoro-N-alkylphthalamic acid and an alkali metal salt of 3-hydroxy-2,4,5-trifluoro-N-alkylbenzamide;

(C) adding a mineral acid to said first aqueous solution to form and precipitate a mixture of 4-hydroxy-3,5,6-trifluoro-N-alkylphthalamic acid and 3-hydroxy-2,4,5-trifluoro-N-alkylbenzamide;

(D) separating said precipitated mixture from said first aqueous solution;

(E) dissolving said precipitated mixture into a first organic solvent to form an organic solution;

(F) heating said solution to convert said 4-methoxy-3,5,6-trifluoro-N-alkylphthalamic acid into 4-methoxy-3,5,6-trifluoro-N-alkylphthalimide;

(G) evaporating said first organic solvent to precipitate a mixture of 4-methoxy-3,5,6-trifluoro-N-alkylphthalimide and 3-methoxy-2,4,5-trifluoro-N-alkylbenzamide;

(H) preparing a second aqueous solution by dissolving said precipitated mixture and an alkali metal hydroxide in water;

(I) adding about 1 to about 2 equivalents of a methylating agent to said second aqueous solution;

(J) heating said second aqueous solution at a temperature of about room temperature to about 50° C. to produce a solution of a mixture of 4-methoxy-3,5,6-trifluoro-N-alkylphthalimide and 3-methoxy-2,4,5-trifluoro-N-alkylbenzamide;

(K) adding a mineral acid to said second aqueous solution to neutralize it;

(L) extracting said 4-methoxy-3,5,6-trifluoro-N-alkylphthalimide and said 3-methoxy-2,4,5-trifluoro-N-alkylbenzamide into a second organic solvent;

(M) separating said second organic solvent from said second aqueous solution;

(N) evaporating said first organic solvent to produce a mixture of solid 4-methoxy-3,5,6-trifluoro-N-alkylphthalamic acid and 3-methoxy-2,4,5-trifluoro-N-alkylbenzamide;

(O) dissolving said mixture from step (N) and an aqueous solution of an acid selected from the group consisting of sulfuric acid, hydrochloric acid, and phosphoric acid at a temperature of about 125° to about 150° C. in water to produce a third aqueous solution containing about 40 to about 60 wt % acid and a mixture of 4-methoxy-3,5,6-trifluorophthalic acid and 3-methoxy-2,4,5-trifluorobenzoic acid;

(P) extracting said mixture of 4-methoxy-3,5,6-trifluorophthalic acid and 3-methoxy-2,4,5-trifluorobenzoic acid into a third organic solvent;

(Q) evaporating said third organic solvent to produce a mixture of solid 4-methoxy-3,5,6-trifluorophthalic acid and 3-methoxy-2,4,5-trifluorobenzoic acid;

(R) dissolving said mixture from step (Q) into an aqueous solution containing a dipolar aprotic decarboxylating solvent to form a fourth aqueous solution; and (S) heating said fourth aqueous solution at a temperature of about 150° to about 180° C. to decarboxylate said 4-methoxy-3,5,6-trifluorophthalic acid and produce 3-methoxy-2,4,5-trifluorobenzoic acid.

14. A method according to claim 13 wherein said alkali metal hydroxide is sodium hydroxide.

15. A method according to claim 13 wherein said methylating agent is dimethyl sulfate.

16. A method according to claim 13 wherein said acid in step (O) is sulfuric acid.

17. A method according to claim 13 wherein said decarboxylating agent is dimethylsulfoxide.

18. A method according to claim 13 wherein said tetrafluorophthalamide is N-methyl tetrafluorophthalimide.

19. A method according to claim 13 wherein said tetrafluorophthalamide is N-phenyl tetrafluorophthalimide.

20. A method according to claim 13 including the additional last step of purifying said 3-methoxy-2,4,5-trifluorobenzoic acid by extracting it into an organic solvent and evaporating said organic solvent.

* * * * *